United States Patent [19]

Kitahara et al.

[11] Patent Number: 5,429,762
[45] Date of Patent: Jul. 4, 1995

[54] COOLING AGENT

[75] Inventors: Koichi Kitahara; Yasuhiko Koiso; Yoshiki Matsumoto; Masayuki Fujisawa; Isao Nagatsu; Mamoru Takahashi, all of Hiratsuka, Japan

[73] Assignee: Japan Pionics Co., Ltd., Tokyo, Japan

[21] Appl. No.: 175,634

[22] Filed: Dec. 30, 1993

[30] Foreign Application Priority Data

Jan. 28, 1993 [JP] Japan .................................. 5-031187

[51] Int. Cl.$^6$ ............................ C09K 5/00; A61F 7/10
[52] U.S. Cl. ............................................. 252/70; 62/4
[58] Field of Search ................... 62/4; 252/70; 165/46; 604/113; 383/901

[56] References Cited

U.S. PATENT DOCUMENTS 3,977,202  8/1976  Forusz et al. ............................... 62/4
5,261,241  11/1993  Kitahara et al. ........................... 62/4

FOREIGN PATENT DOCUMENTS 2011057  7/1979  United Kingdom .

OTHER PUBLICATIONS

Patent Abstracts of Japan, vol. 15, No. 31 (C-0798), 24 Jan. 1991, of JP-A-22 069 180, 2 Nov. 1990.
Patent Abstracts of Japan, vol. 14, No. 220 (C-0717), 10 May 1990, of JP-A-20 051 581, 21 Feb. 1990.
Patent Abstracts of Japan, vol. 6, No. 68 (C-100), 30 Apr. 1982, of JP-A-57 005 784, 12 Jan. 1982.

*Primary Examiner*—Mark L. Bell
*Assistant Examiner*—C. M. Bonner
*Attorney, Agent, or Firm*—Frishauf, Holtz, Goodman & Woodward

[57] ABSTRACT

A cooling agent which cools by an endothermic reaction resulting from the dissolving of crystals of inorganic salts water, the salts crystallizing at about room temperature by supplying heat. The cooling agent comprises a mixture of (i) a sodium phosphate salt, (ii) a sodium ammonium phosphate salt or an ammonium phosphate salt, and (iii) water. The cooling agent is produced in a manner which avoids the conglomeration of the crystals, which was a difficulty in the art. Moreover, the cooling agent of the present invention can be used repeatedly. When a nucleating agent, a highly water absorbent polymer or a thickener is added to the cooling agent, the precipitation of the crystals occurs in a still finer and stabler state. The cooling agent can be used in a cooling pillow having a desirable cooling property and a soft and agreeable touch, which offers comfort with safety and which is free from conglomeration of crystals, even after a long period of time.

18 Claims, No Drawings

COOLING AGENT

BACKGROUND OF THE INVENTION

1. Field of the Invention

The present invention relates to a cooling agent and more particularly pertains to a cooling agent having an excellent cooling property and an agreeable touch, free from conglomerating in the state of a crystal. The present invention provides a cooling product that does not suffer from an unagreeable feel or breakage of the covering bag when used for cooling down the head or an affected parts area of a user of the cooling product, but has a high comfortability and safety. The prevent invention concerns a cooling pillow utilizing the cooling agent.

2. Description of the Related Art

Heretofore, in order to cool down the head and affected area of a person, ice-bags or water pillows and the like have conventionally been used.

Lately, cooling pillows utilizing an endothermic phenomena caused from dissolution of crystals of inorganic salts into water as a solvent have been employed, and as the content thereof, cooling agent therefor have comprised sodium sulfate and water or disodium hydrogenphosphate and water in combination (Japanese Utility Model Publication No. 21809/1992).

Ice-bags and water pillows are, however, generally large in weight, and suffer from many inconveniences including the necessity of preparing ice or cold water for every use.

Cooling agents comprising sodium sulfate and water or disodium hydrogenphosphate and water in combination are superior in convenience to ice bags and water pillows, but have many defects. Once they are dissolved and then recrystallize, the crystals become larger in particle size and result in poor touch when used and cause discomfort. Further, the crystals conglomerate when left as they are, and the resulting stiff crystals sometimes break the bag containing the cooling agent by shock or the like.

SUMMARY OF THE INVENTION

To overcome these problems, the present inventors repeated investigations to obtain a safe cooling agent agreeable to the touch and feel free from conglomerating at crystallization. The present inventors consequently found that these problems can be overcome by using sodium phosphate salt and sodium ammonium phosphate salt or ammonium phosphate salt, in combination, as the inorganic salts crystallize at around room temperature. Thus, the present invention has been attained.

That is, the present invention relates to a cooling agent, utilizing the endothermic phenomena caused by dissolution of inorganic salts crystals into water as the solvent owing to the rise in temperature at around room temperature, comprises (i) a sodium phosphate salt, (ii) a sodium ammonium phosphate salt or ammonium phosphate salt, and (iii) water, and also a cooling pillow using the same.

DESCRIPTION OF PREFERRED EMBODIMENT

In the cooling agent of the present invention, sodium-containing phosphate salts and ammonium-containing phosphate salts are used in combination, as the inorganic salts for the cooling agent mixed with water, and usually sealed in a flat bag and the like to be put into practical use.

Examples of sodium phosphate salts to be used in the present invention are disodium hydrogenphosphate ($Na_2HPO_4$), $12H_2O$ hydrate thereof and the like, sodium dihydrogenphosphate ($NaH_2PO_4$), $2H_2O$ hydrate thereof and the like, trisodium phosphate ($Na_3PO_4$), and $10H_2O$ hydrate thereof and the like. Among them, preferred are disodium hydrogenphosphate and hydrates thereof as the main component.

Sodium ammoniumphosphate salts or ammonium phosphate salts to be used in combination with the above-mentioned sodium phosphate salts are, for example, sodium ammonium hydrogenphosphate ($NaNH_4HPO_4$), $4H_2O$ hydrate thereof, diammonium hydrogenphosphate [$(NH_4)_2HPO_4$], ammonium dihydrogenphosphate ($NH_4H_2PO_4$), triammonium phosphate [$(NH_4)_3PO_4$], and hydrates thereof. Among them, preferred are sodium ammonium hydrogenphosphate, diammonium hydrogenphosphate, and hydrates thereof as the main component.

Generally, cooling agents are prepared by mixing a sodium phosphate salt and a sodium ammonium hydrogenphosphate salt or an ammonium phosphate salt itself as mentioned above with water, or by heat dissolving and then recrystallizing them, but mostly the former method are adopted. Or an acid, an alkali and a salt which react in water to produce them may be mixed and used as a cooling agent.

For example, to produce sodium phosphate salts containing disodium hydrogenphosphate as the main component, used are (i) a method of neutralizing phosphoric acid with caustic soda or sodium carbonate, or (ii) a method of adding phosphoric acid to the aqueous solution of anhydrous sodium phosphate salts such as trisodium triphosphate ($Na_3P_3O_9$), trisodium phosphate ($Na_3PO_4$), sodium dihydrogenphosphate ($NaH_2PO_4$), sodium pyrophosphate ($Na_4P_2O_7$), disodium dihydrogenpyrophosphate ($Na_2H_2P_2O_7$), sodium methaphosphate [$(NaPO_3)n$], sodium tripolyphosphate ($Na_5P_3O_{10}$) and hydrate-containing salts thereof.

To prepare ammonium salts containing sodium ammonium hydrogenphosphate salts as the main component, for example, (i) a method of adding ammonium chloride to the aqueous solution of disodium hydrogenphosphate, (ii) a method of adding caustic soda to the aqueous solution of anhydrous phosphate salt such as ammonium dihydrogenphosphate, diammonium hydrogenphosphate, triammonium phosphate and hydrate-containing salts thereof, and (iii) a method of preparing ammonium phosphate salts from phosphoric acid and aqueous ammonia, and further taking the above-mentioned step (ii) are adopted.

In these methods, depending on the conditions for preparation, also other sodium phosphate salts or ammonium phosphate sometimes are produced in a mixed state, but they can be used as it is as the cooling agent.

In the cooling agent of the present invention, the concentration and compounding proportions of the salts are selected so that crystals will be precipitated in a lower range of room temperature, that is, at a temperature of 10° to 25° C., and the precipitated crystal can be dissolved with the endothermic phenomena in a temperature range where the temperature of it is raised by the person's temperature and the like, that is, for example, a temperature of 25° to 30° C.

The amount by weight of the salts in total of sodium phosphate salts and sodium ammonium phosphate salts or ammonium phosphate salts is, if the amount in total of the salts in aqueous solution and in the form of the precipitating crystal, as an anhydride thereof, is usually 5 to 60% by weight, preferably 15 to 35% by weight, and still more preferably 20 to 30% by weight of whole the amount of the cooling agent.

If the amount by weight of salts is lower than 5% by weight, it is difficult for them to recrystallize at room temperature, while if it is larger than 60% by weight, the amount of crystal is so large that the touch of the cooling agent may be unfavorably lowered.

The proportion of the sodium ammonium hydrogenphosphate and the ammonium phosphate salts to the sodium phosphate salt is not particularly limited, but the ratio of Na to $NH_4$ group ($Na/NH_4$) contained in whole the phosphate in the cooling agent is usually 1:5 to 5:1, preferably 1:1 to 5:1 in molar ratio, and the total molar ratio of Na and $NH_4$ group to 1 mol of $PO_4$ group, that is, $[(Na+NH_4)PO_4]$ is usually 1:1.5 to 1:2.5, preferably 1:1.8 to 1:2.2. If the ratio of Na and $NH_4$ group and $PO_4$ group is too distant from these ranges, there is the possibility that the crystalline particles become too large, or conglomerate, or the pH of the solution becomes 10 or more or 4 or less, which causes problems in safety in handling at production.

In the present invention, for the purpose of controlling the amount of precipitating crystal and the dissolution temperature of the cooling agent, in addition to the above-mentioned salts, other salts can be used in combination, if necessary. For example, sodium carbonate, sodium hydrogencarbonate, potassium sodium carbonate, sodium chrome carbonate, sodium scandium carbonate, sodium cerium carbonate, and sodium sulfate, and hydrates thereof can be used.

In the present invention, it is preferred to add a nucleating agent to help the precipitation of the crystals.

As a nucleating agent, phosphates or hydroxides of the metals such as lithium and alkaline earth metals, and hydrates of these compounds are used.

The phosphates include strontium phosphates, lithium phosphates, calcium phosphates, barium phosphates, and magnesium phosphates, and hydrates thereof. Specific examples of them are trilithium phosphate, dilithium hydrogenphosphate, lithium dihydrogenphosphate, tristrontium diphosphate, strontium hydrogenphosphate, strontium tetrahydrogendiphosphate, tricalcium diphosphate, calcium hydrogenphosphate, calcium tetrahydrogendiphosphate, trimagnesium diphosphate, magnesium hydrogenphosphate, magnesium tetrahydrogendiphosphate, tribarium diphosphate, barium hydrogenphosphate, barium tetrahydrogendiphosphate, and hydrates thereof. Besides the above, pyrophosphates which are hydrolyzed in water to produce these salts are also effective.

The hydroxides includes strontium hydroxide, calcium hydroxide, lithium hydroxide, barium hydroxide, and magnesium hydroxide, and hydrates thereof.

Among them, calcium phosphates, strontium phosphates, calcium hydroxide, and strontium hydroxide, and hydrates thereof are preferable, and calcium hydrogenphosphate, strontium hydrogenphosphate, strontium hydroxide, and hydrates thereof are particularly preferable. These may be used alone, or two or more of them may be used in combination.

By adding and mixing these nucleating agents, usually fine and stable precipitation of crystals is obtained. When a hydroxide is used, however, it is preferably heated to about 80° C. once after added, then cooled, and thus made into a still finer crystalline precipitation before being used.

The amount of the nucleating agent is 0.01 to 5% by weight, preferably 0.05 to 3% by weight of the whole amount of the cooling agent.

In the present invention, it is preferred to add a highly water absorbent polymer, thickener, and/or polymeric flocculant for the purpose of preventing the cooling agent from conglomerating, constantly maintaining it in a state of fine crystals to offer a soft touch, and at the same time heightening the safety so that the chemical solution may not scatter onto a human body even if the bag is broken.

The highly water absorbent polymer includes, for example, polyacrylic acid, starch-acrylic acid graft copolymer, maleic acid copolymer, polyvinyl alcohol, and an isobutylene-maleic acid copolymer. The thickener includes, for example, xanthan gum (polysaccharide), carboxymethylcellulose, sepiolite clay and the like. As the polymeric flocculant, any of cationic, artionic, non-ionic, ampho-ionic (including betainic ampho-ionic) ones can be used. Specific example of them are polymethacrylic acid ester, polyallyl amine, polyacrylamide, chitosan, polyacrylic soda, acrylamide-acrylic soda copolymer, partially hydrolyzed polyacrylamide, polyethyleneoxide and the like. These may be used alone, or two or more of them may be used in combination.

Among them, highly water absorbent polymers and polysaccharide-based thickeners are preferable, and preferable examples of the former are polyacrylic highly water absorbent polymers such as SANWET IM-500D, and SANFRESH ST-500MPS (produced by SANYO CHEMICAL INDUSTRIES,LTD.), AQUALIC CS 6S, and AQUALIC CS 6HM (produced by NIPPON SHOKUBAI CO.,LTD.), particularly those in fine particles such as SANFRESH ST-500MPS and AQUALIC CS 6S, and preferable examples of the latter are KELZAN (xanthan gum produced by KELCO DIVISION OF MERCK & CO., INC. U.S.)

The amount of them to be added is usually 0.01 to 3% by weight, preferably 0.1 to 2% by weight of the whole amount of the cooling agent.

The present invention further relates to a cooling pillow using the above-mentioned cooling agent.

A cooling pillow herein means a cooling pillow, in the general sense, which comprises the above-mentioned cooling agent sealed in a water-penetration resistant bag, and which is to be applied on a hot part to cool said part, and is effectively utilized as a cooling bag to cool down affected parts, and as a temperature-controlling means fixed on the warm part of industrial equipment, as well as the usual use as a cooling pillow for men.

As the material for the bag which contains the cooling agent, synthetic resin films of polyethylene, polypropylene, polyester, nylon, polyvinyl chloride, polyvinylidene chloride, and polyisocyanate and the like, and combined films thereof can be used. Among them, films of polyvinyl chloride, nylon and combination thereof are preferable in view of strength, flexibility, processability and cost.

Cooling pillows are usually made by putting the cooling agent into a flat bag, but in the case of a cooling pillow for men, for the purpose of providing superior touch, realizing comfortable sleep, and enhancing the recovery from fatigue, both or one side of the outer surface of the synthetic resin film bag may be covered with, or laminated by absorbent cotton, gauze, nonwoven fabric made of water-absorbing fiber layer, or fiber-planted cloth with a water-absorbing fiber layer planted on it.

The flat bag which contains the cooling agent is used as a cooling pillow, as it is, or is further covered with a soft covering material, or contained in a thick pillow provided with a containing part such as a pocket.

The size and shape of the flat bag are not particularly limited, but are sufficient to be as large as the bag has an area size enough to be applied for the above-mentioned purposes. The shape of it may be any of rectangle, square, circle, oval and the like.

Cooling pillows or cooling bags thus obtained are used in the state in which a large amount of fine crystals are precipitated out at a temperature of 10° to 25° C. The cooling agent absorbs heat from the head of the patient while cooling it, and the rise in the temperature of it owing to the absorption dissolves the crystal again. During the dissolution, since absorption of heat caused by dissolution is maintained, a desired temperature of 25° to 30° C. is maintained to offer favorable feel for a long period of time. After they are used, the pillow or bag can be further used repeatedly, for the cooling agent crystallizes again when they are left under a low temperature atmosphere of 10° to 25° C.

The cooling agent of the present invention is obtained from the co-use of a sodium phosphate salt and an ammonium phosphate salt, and is free from conglomerating of crystal which has been a defect of the prior art. Thus, it can be repeatedly used for many times.

If a nucleating agent, a highly water absorbent polymer, or a thickener is added to the cooling agent, a still stabler state of finer crystal precipitation is maintained.

Accordingly, said cooling agent, in an application to cooling pillows and the like, has an excellent cooling agent property and offers soft and favorable touch, comfortability with safety, without the fear of conglomerating of crystals even being left for a long period of time, and can be used repeatedly with safety.

EXAMPLE 1

Two sheets of colorless semitransparent soft polyvinyl chloride film with a thickness of 90 μm cut to the size of 220×240 mm were overlapped, three sides of which were high-frequency stitched each in the width of 5 mm to make a flat bag with one side open.

Into said bag, was placed a cooling agent which was obtained by adding ion-exchanged water to 162 g, as an anhydride, of disodium hydrogenphosphate, and 162 g, as an anhydride, of sodium ammonium hydrogenphosphate to make a mixture of 1300 g in total, and the open side was sealed by high-frequency stitching to obtain a cooling pillow.

Said cooling pillow was immersed in a thermostat water bath of 30° C., and the crystals therein were dissolved. Thereafter, the cooling pillow was left in a room at 10° C. overnight, and crystals were precipitated again. Said crystals were fine and in a slurry state, and the whole pillow was soft and had a favorable touch.

Subsequently, one side surface of the above cooling pillow was made to closely contact with the outer wall of the thermostat water bath kept at 30° C., a thermocouple thermometer was set onto the other side surface, which was covered all over with three-fold flannel, firmly fixed with sticky tape, and the change in the temperature was measured.

As the result, the temperature of the pillow rose while the crystals dissolved little by little. The favorable temperature for a comfortable pillow was maintained for a long period of time as about 8 hours corresponding to the change in the temperature from 10° C. to 25° C., and 14 hours in total till the temperature reached 28° C.

The sample was left in a room at 10° C. again to precipitate crystals, and the state was observed. As the result, the crystals was found to be fine, and the cooling agent was in a slurry state. The sample was left as it was for one week, but the state hardly changed, and no conglomeration or the like was observed.

As the result of further observation, crystals with a particle diameter of 3 to 6 mm were found in some parts only after 5 days.

EXAMPLE 2

A sample of a cooling pillow was made in the same manner as in Example 1 except for using a cooling agent prepared by adding ion-exchanged water to 240 g, as an anhydride, of disodium hydrogenphosphate and 78 g, as an anhydride, of diammonium hydrogenphosphate to make a mixture of 1300 g in total.

As the result of carrying out a test on the sample under the same conditions as in Example 1, a favorable temperature was maintained for a long period of time while the crystals were dissolved little by little as about 8 hours, and 14 hours in total till the temperature reached 25° C. and 28° C., respectively.

The sample was left in a room at 10° C. again, and observed for the state. As the result, the crystals were fine and the refrigerant was in the state of slurry. The sample was left as it was for one week, but the state hardly changed, and no conglomeration or the like was observed.

As the result of further observation, crystals with a particle diameter of 3 to 6 mm were found in some parts only after 7 days.

EXAMPLE 3

A sample of a cooling pillow was made in the same manner as in Example 1 except for using a cooling agent prepared by adding ion-exchanged water to 200 g, as an anhydride, of disodium hydrogenphosphate, 36 g, as an anhydride, of sodium ammonium hydrogenphosphate, and 35 g, as an anhydride, of diammonium hydrogenphosphate to make a mixture of 1300 g in total.

As the result of carrying out a test on said sample under the same conditions as in Example 1, favorable temperature was maintained for a long period of time while the crystals were dissolved little by little as about 8 hours, and 14 hours in total till the temperature reached 25° C. and 28° C., respectively.

The sample was left in a room at 10° C. again, and observed for the state. As the result, the crystals were fine and the cooling agent was in the state of slurry. The sample was left as it was for one week, but the state hardly changed, and no conglomeration or the like was observed.

As the result of further observation, crystals with a particle diameter of 4 to 8 mm were found in some parts only after 5 days.

EXAMPLE 4

A sample of a cooling pillow was made in the same manner as in Example 1 except for using a cooling agent prepared by adding ion-exchanged water to 240 g, as an anhydride, of disodium hydrogenphosphate, 78 g, as an anhydride, of diammonium hydrogenphosphate, and, in addition, 1 g of strontium hydroxide as a nucleating agent to make a mixture of 1300 g in total.

As the result of carrying out a test on said sample under the same conditions as in Example 1, favorable temperature was maintained for a long period of time while the crystals were dissolved little by little as about 8 hours, and 14 hours in total till the temperature reached 25° C. and 28° C., respectively.

The sample was left in a room at 10° C. again, and observed for the state. As the result, fine needle-like crystals were precipitated out, and the cooling agent was in the state of a slurry. The sample was left as it was for one week, but the state hardly changed. Also after 3 months, the state hardly changed too, and no conglomeration or the like was observed.

As the result of further observation, crystals with a particle diameter of 4 to 8 mm were found in some parts only after 15 days.

EXAMPLE 5

A sample of a cooling pillow was made in the same manner as in Example 1 except for using a cooling agent prepared by adding ion-exchanged water to 240 g, as an anhydride, of disodium hydrogenphosphate, 78 g, as an anhydride, of diammonium hydrogenphosphate, and, in addition, 2 g of lithium hydroxide as the nucleating agent to make a mixture of 1300 g in total.

As the result of carrying out a test on said sample under the same conditions as in Example 1, favorable temperature was maintained for a long period of time while the crystals were dissolved little by little as about 8 hours, and 14 hours in total till the temperature reached 25° C. and 28° C., respectively.

The sample was left in a room at 10° C. again, and observed for the precipitating state of crystal. As the result, fine crystals were precipitated, and the cooling agent as the whole came to be in the state of a slurry. The sample was left as it was for one week, but the state hardly changed. Also after three months, it hardly changed, and no conglomeration or the like was observed.

As the result of further observation, crystals with a particle diameter of 3 to 6 mm were found in some parts only after one month.

EXAMPLE 6

A sample was made in the same manner as in Example 1 except for using a cooling agent prepared by adding ion-exchanged water to 240 g, as an anhydride, of disodium hydrogenphosphate, 78 g, as an anhydride, of diammonium hydrogenphosphate, and, in addition, 2 g of dihydrate of calcium hydrogenphosphate as the nucleating agent to make a mixture of 1300 g in total.

As the result of carrying out a test under the same conditions as in Example 1, favorable temperature was maintained for a long period of time while the crystals were dissolved little by little as about 8 hours, and 14 hours in total till the temperature reached 25° C. and 28° C., respectively.

The sample was left in a room at 10° C. again, and observed for the precipitating state of crystals. As the result, numerous fine crystals were precipitated, and the cooling agent as a whole became a slurry. The sample was left as it was for one week, but the state hardly changed. Also after 3 months, the state hardly changed, and no conglomeration or the like was observed.

As the result of further observation, crystals with a particle diameter of 3 to 6 mm were found in some parts only after 1 month.

EXAMPLE 7

A sample was made in the same manner as in Example 1 except for using a cooling agent prepared by adding ion-exchanged water to 240 g, as an anhydride, of disodium hydrogenphosphate, 78 g, as an anhydride, of diammonium hydrogenphosphate, and in addition 2 g of dihydrate of calcium hydrogenphosphate as the nucleating agent, and 9 g of SANWET IM-500D (produced by SANYO CHEMICAL INDUSTRIES, LTD.) as the highly water absorbent polymer to make a mixture of 1300 g in total.

As the result of carrying out a test on said sample under the same conditions as in Example 1, favorable temperature was maintained for a long period of time while the crystals were dissolved little by little as about 8 hours, and 14 hours in total till the temperature reached 25° C. and 28° C., respectively.

The sample was left in a room at 10° C. again, and observed for the precipitating state of crystals. As a result, numerous fine crystals were precipitated, and the cooling agent as the whole became a somewhat viscous slurry, and the sample had a soft touch. The sample was left as it was for one week, but the state hardly changed. As the result of similar observations after 3 months and 6 months, the state hardly changed, and no conglomeration was observed.

After further observation, crystals with a particle diameter of 3 to 6 mm were found in some parts only after 1 month.

EXAMPLE 8

A sample was made in the same manner as in Example 1 except for using a cooling agent prepared by adding ion-exchanged water to 120 g, as an anhydride, of sodium phosphate, 120 g, as an anhydride, of ammonium dihydrogenphosphate, and in addition 2 g of dihydrate of calcium hydrogenphosphate as the nucleating agent, and 6 g of SANFRESH ST-500MPS (fine powder-type, produced by SANYO CHEMICAL INDUSTRIES, LTD.) as the highly water absorbent polymer to make a mixture of 1300 g in total.

As the result of carrying out a test on said sample under the same conditions as in Example 1, favorable temperature was maintained for a long period of time while the crystals were dissolved little by little as about 9 hours, and 16 hours in total till the temperature reached 25° C. and 30° C., respectively.

The sample was left in a room at 10° C. again, and observed for the precipitating state of crystals. As the result, numerous fine crystals were precipitated, and the cooling agent as whole became a somewhat viscous slurry, and the sample had a soft touch. The sample was left as it was for one week, but the state hardly changed. As the result of similar observations after 3 months, and 9 months, the state hardly changed, and no conglomeration was observed.

After further observation, crystals with a particle diameter of 4 to 8 mm were found in some parts only after 1 month.

EXAMPLE 9

A sample was made in the same manner as in Example 1 except for using a cooling agent prepared by adding ion-exchanged water to 240 g, as an anhydride, of disodium hydrogenphosphate, 78 g, as an anhydride, of diammonium hydrogenphosphate, and in addition 2 g of dihydrate of calcium hydrogenphosphate as the nucleating agent, and 9 g of SANFRESH ST-500MPS (produced by SANYO CHEMICAL INDUSTRIES, LTD.) as the highly water absorbent polymer to make a mixture of 1300 g in total.

As the result of carrying out a test on said sample under the same conditions as in Example 1, favorable temperature was maintained for a long period of time while the crystals were dissolved little by little as about 9 hours, and 16 hours in total till the temperature reached 25° C. and 30° C., respectively.

The sample was left in a room at 10° C. again, and observed for the precipitating state of crystals. As the result, numerous fine crystals were precipitated, and the cooling agent as a whole became a somewhat viscous slurry, and the sample had a soft touch. The sample was left as it was for one week, but the state hardly changed. As the result of similar observations after 3 months, 6 months and 9 months, the state hardly changed, and no conglomeration was observed.

EXAMPLE 10

A sample was made in the same manner as in Example 1 except for using a cooling agent prepared by adding ion-exchanged water to 240 g, as an anhydride, of disodium hydrogenphosphate, 78 g, as an anhydride, of diammonium hydrogenphosphate, and in addition 2 g of dihydrate of calcium hydrogenphosphate as the nucleating agent, and 7 g of KELZAN (xanthan gum, produced by KELCO DIVISION OF MERCK & CO., INC. U.S.) as the thickener to make a mixture of 1300 g in total.

As the result of carrying out a test on said sample under the same conditions as in Example 1, favorable temperature was maintained for a long period of time while the crystals were dissolved little by little as about 8.5 hours, and 15.5 hours in total till the temperature reached 25° C. and 30° C., respectively.

The sample was left in a room at 10° C. again, and observed for the precipitating state of crystals. As the result, numerous fine crystals were precipitated, and the cooling agent as a whole became somewhat a viscous slurry, and the sample had a soft touch. The sample was left as it was for one week, but the state hardly changed. As the result of similar observations after 3 months, 6 months and 9 months, the state hardly changed, and no conglomeration was observed.

EXAMPLE 11

A sample of cooling pillow was made in the same manner as in Example 1 except for using a cooling agent prepared by adding ion-exchanged water to 194 g, as an anhydride, of sodium dihydrogenphosphate, 65 g of sodium hydroxide, 78 g, as anhydride, of diammonium hydrogenphosphate, and in addition 1 g of strontium hydroxide as the nucleating agent to make a mixture of 1300 g in total.

As the result of carrying out a test on said sample under the same conditions as in Example 1, favorable temperature was maintained for a long period of time while the crystals were dissolved little by little as about 8 hours, and 15 hours in total till the temperature reached 25° C. and 30° C., respectively.

The sample was left in a room at 10° C. again, and observed for the precipitating state of crystals. As the result, fine needle-like crystals were precipitated, and the cooling agent as a whole became a slurry. The sample was left as it was for one week, but the state hardly changed, and no conglomeration and the like was observed.

As the result of similar observations after 3 months, the state hardly changed. Fifteen days after that, crystals with particle diameter of 4 to 8 mm were first observed in some parts.

EXAMPLE 12

A sample of cooling pillow was made in the same manner as in Example 1 except for using a cooling agent prepared by adding ion-exchanged water to 185 g, as an anhydride, of trisodium phosphate, 55 g of phosphoric acid, 78 g, as an anhydride, of diammonium hydrogenphosphate, and in addition 2 g of calcium hydroxide as the nucleating agent to make a mixture of 1300 g in total.

As the result of carrying out a test on said sample under the same conditions as in Example 1, favorable temperature was maintained for a long period of time while the crystals were dissolved little by little as about 8.5 hours, and 15.5 hours in total till the temperature reached 25° C. and 30° C., respectively.

The sample was left in a room at 10° C. again, and observed for the precipitating state of crystals. As the result, fine crystals were precipitated, and a cooling agent as the whole became slurry. The sample was left as it was for one week, but the state hardly changed, and no conglomeration and the like was observed.

As the result of similar observations after 3 months, the state hardly changed, and no conglomeration was observed. One month after that, crystals with particle diameter of 4 to 8 mm were first observed in some parts.

COMPARATIVE EXAMPLE 1

A sample was made in the same manner as in Example 1 except for using a cooling agent prepared by adding ion-exchanged water to 324 g, as an anhydride, of disodium hydrogenphosphate to make a mixture of 1300 g in total.

As the result of carrying out a test on said sample under the same conditions as in Example 1, the temperature of the sample reached 25° C. after about 4 hours, and 28° C. after 10 hours.

After the observation of the state of the recrystallization in the same manner as in Examples, a large number of comparatively large crystals with particle diameter of 6 to 12 mm were produced. The sample was left as it was for one week, and then the crystals had grown to form conglomerations, which could not be broken by simple pressing with one's fingers.

COMPARATIVE EXAMPLE 2

A sample was made in the same manner as in Example 1 except for using a cooling agent prepared by adding ion-exchanged water to 380 g, as an anhydride, of sodium sulfate to make a mixture of 1300 g in total.

As the result of carrying out a test on said sample under the same conditions as in Example 1, the temperature of the sample reached 25° C. after about 2 hours, and 28° C. after 6 hours.

After the observation of the state of the recrystallization in the same manner as in Examples, a great number of conglomerations of crystals still larger than those of Comparative Example 1 had grown up. These could not be broken by a striking with one's hands, and a stronger strike broke the bag to let the solution leak out.

What is claimed is:

1. A cooling agent which cools by an endothermic phenomena caused by the dissolution of an inorganic salt crystal in water as a solvent, said dissolving occurring by a rise in temperature at about room temperature, the cooling agent comprising a mixture of (i) a sodium phosphate salt, (ii) a sodium ammonium phosphate salt or an ammonium phosphate salt, and (iii) water, wherein the cooling agent contains a molar ratio of Na to $NH_4$ groups of 1:5 to 5:1 and a total molar ratio of Na and $NH_4$ groups to 1 mol of $PO_4$ groups of 1:1.5 to 1:2.5.

2. The cooling agent as defined in claim 1 wherein the sodium phosphate salt is at least one salt selected from the group consisting of disodium hydrogenphosphate, sodium dihydrogenphosphate, trisodium phosphate, and hydrates thereof.

3. The cooling agent as defined in claim 1 wherein said (ii) is at least one salt selected from the group consisting of sodium ammonium hydrogenphosphate, diammonium hydrogenphosphate, ammonium dihydrogenphosphate, ammonium phosphate and hydrates thereof.

4. The cooling agent as defined in claim 1 wherein the sodium phosphate salt is disodium hydrogenphosphate or the hydrate thereof, and the sodium ammonium phosphate salt or ammonium phosphate salt is sodium ammonium hydrogenphosphate or diammonium hydrogenphosphate or the hydrates thereof.

5. The cooling agent as defined in claim 1 which further comprises 0.01 to 5% by weight, based on the weight of the cooling agent, of at least one nucleating agent selected from the group consisting of a phosphate of lithium, a hydroxide of lithium, a phosphate of an alkaline earth metal, a hydroxide of an alkaline earth metal and hydrates thereof.

6. The cooling agent as defined in claim 5 wherein the nucleating agent is calcium phosphate salt, strontium phosphate salt, calcium hydroxide, strontium hydroxide, or hydrates thereof.

7. The cooling agent as defined in claim 1 which further comprises one additive selected from the group consisting of a highly water absorbent polymer, a thickener, and a polymeric flocculant, in an amount of 0.01 to 3% by weight based on the weight of the cooling agent.

8. A cooling agent which cools by an endothermic phenomena caused by the dissolution of an inorganic salt crystal in water as a solvent, said dissolving occurring by a rise in temperature at about room temperature, the cooling agent comprising a mixture of (i) a sodium phosphate salt, (ii) a sodium ammonium phosphate salt or an ammonium phosphate salt, and (iii) water, wherein the phosphate salts (i) and (ii) are contained in the cooling agent in an amount of 5 to 60% by weight, determined as an anhydride.

9. The cooling agent as defined in claim 8 wherein the sodium phosphate salt is at least one salt selected from the group consisting of disodium hydrogenphosphate, sodium dihydrogenphosphate, trisodium phosphate and hydrates thereof.

10. The cooling agent as defined in claim 8 wherein said (ii) is at least one salt selected from the group consisting of sodium ammonium hydrogenphosphate, diammonium hydrogenphosphate, ammonium dihydrogenphosphate, ammonium phosphate and hydrates thereof.

11. The cooling agent as defined in claim 8 wherein the sodium phosphate salt is disodium hydrogenphosphate or the hydrate thereof, and the sodium ammonium phosphate salt or ammonium phosphate salt is sodium ammonium hydrogenphosphate or diammonium hydrogenphosphate or hydrates thereof.

12. The cooling agent as defined in claim 8 which further comprises 0.01 to 5% by weight, based on the weight of the cooling agent, of at least one nucleating agent selected from the group consisting of a phosphate of lithium, a hydroxide of lithium, a phosphate of an alkaline earth metal, a hydroxide of an alkaline earth metal and hydrates thereof.

13. The cooling agent as defined in claim 12 wherein the nucleating agent is selected from the group consisting of calcium phosphate salt, strontium phosphate salt, calcium hydroxide, strontium hydroxide, and hydrates thereof.

14. The cooling agent as defined in claim 8 which further comprises one additive selected from the group consisting of a highly water absorbent polymer, a thickener, and a polymeric flocculant, in an amount of 0.01 to 3% by weight based on the weight of the cooling agent.

15. The cooling agent as defined in claim 8 wherein the phosphate salts (i) and (ii) are contained in the cooling agent in an amount of 15 to 35% by weight, determined as an anhydride.

16. The cooling agent as defined in claim 8 wherein the phosphate salts (i) and (ii) are contained in the cooling agent in an amount of 20 to 30% by weight, determined as an anhydride.

17. The cooling agent as defined in claim 1 wherein the cooling agent contains a molar ratio of Na to $NH_4$ groups of 1:1 to 5:1 and a total molar ratio of Na and $NH_4$ groups to 1 mol of $PO_4$ groups of 1:1.8 to 1:2.2.

18. A cooling pillow which comprises the cooling agent as defined in any of claims 2, 3, 4, 5, 6, 7, 1, 8, 9, 10, 11, 12, 13, 14, 15, 16 or 17 sealed in a synthetic resin bag.

* * * * *